United States Patent [19]

Angerbauer et al.

[11] Patent Number: 5,064,841
[45] Date of Patent: Nov. 12, 1991

[54] HMG-COA REDUCTASE-INHIBITING IMINO-SUBSTITUTED PYRIDINES

[75] Inventors: Rolf Angerbauer; Peter Fey; Walter Hübsch, all of Wuppertal; Thomas Philipps, Koeln; Hilmar Bischoff, Wuppertal; Dieter Petzinna, Duesseldorf; Delf Schmidt, Wuppertal, all of Fed. Rep. of Germany

[73] Assignee: Bayer Aktiengesellschaft, Leverkusen, Fed. Rep. of Germany

[21] Appl. No.: 558,029

[22] Filed: Jul. 26, 1990

[30] Foreign Application Priority Data

Aug. 3, 1989 [DE] Fed. Rep. of Germany ....... 3925636

[51] Int. Cl.$^5$ .................... A61K 31/44; C07D 405/06
[52] U.S. Cl. .................................. 514/336; 514/357; 546/268; 546/335
[58] Field of Search ............... 546/268, 335; 514/336, 514/357

[56] References Cited

U.S. PATENT DOCUMENTS

| | | | |
|---|---|---|---|
| 4,906,624 | 3/1990 | Chucholowski et al. | 546/187 |
| 4,950,675 | 8/1990 | Chucholowski | 546/268 |
| 4,968,689 | 11/1990 | Angerbauer | 546/268 |

*Primary Examiner*—Jane T. Fan
*Attorney, Agent, or Firm*—Sprung Horn Kramer & Woods

[57] ABSTRACT

HMG-CoA reductase-inhibiting imino-substituted pyridines of the formula

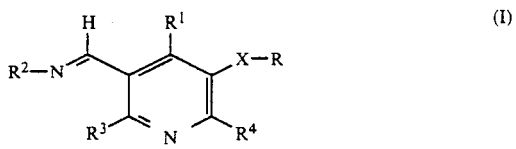

in which
$R^1$ is optionally substituted aryl,
$R^2$ is optionally substituted aryl or alkyl, OH, alkoxy, aralkoxy, or optionally substituted aryloxy,
$R^3$ is cycloalkyl, or optionally substituted aaryl or alkyl,
$R^4$ is alkyl or cycloalkyl,
X is —CH$_2$—CH$_2$— or ≦CH═CH—,
R is

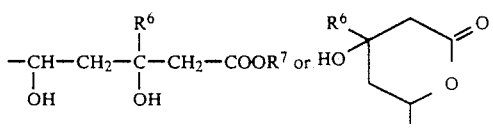

$R^6$ is H or alkyl, and
$R^7$ is H, alkyl, phenylalkyl, aryl or a cation, and their salts.

10 Claims, No Drawings

HMG-COA REDUCTASE-INHIBITING IMINO-SUBSTITUTED PYRIDINES

The invention relates to imino-substituted pyridine, to intermediate compounds for their preparation, and to their preparation and their use in medicaments.

It is known that lactose derivatives isolated from fungal cultures are inhibitors of 3-hydroxy-3-methyl-glutaryl-coenzyme A reductase (HMG-CoA reductase) [mevinolin, EP-A 22,478; U.S. Pat. No. 4,231,938]. In addition, substituted pyridines are described in DOS 3,801,406. Furthermore, 3-desmethyl-mevalonic acid derivatives are known (compare DE 3,823,045 A 1).

Imino-substituted pyridines of the general formula (I)

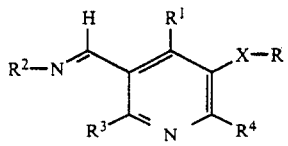

in which $R^1$ represents aryl having 6 to 10 carbon atoms, which is optionally monosubstituted to trisubstituted by identical or different substituents from the series comprising halogen, hydroxyl, trifluoromethyl, trifluoromethoxy, nitro, cyano, straight-chain or branched alkyl or alkoxy in each case having up to 8 carbon atoms or by aryloxy having 6 to 10 carbon atoms, $R^2$ represents aryl having 6 to 10 carbon atoms, which is optionally monosubstituted to trisubstituted by identical or different substituents from the series comprising straight-chain or branched alkyl in each case having up to 8 carbon atoms, halogen, cyano, trifluoromethyl, trifluoromethoxy and nitro, or represents straight-chain or branched alkyl having up to 10 carbon atoms, which is optionally substituted by aryl having 6 to 10 carbon atoms, hydroxyl or alkoxy having up to 8 carbon atoms, or represents a group of the formula —OR$^5$, in which $R^5$ denotes hydrogen or straight-chain or branched alkyl having up to 8 carbon atoms, which is optionally substituted by aryl having 6 to 10 carbon atoms, or denotes aryl having 6 to 10 carbon atoms, which is optionally substituted by straight-chain or branched alkyl or alkoxy in each case having up to 8 carbon atoms, halogen, nitro, cyano, trifluoromethyl or trifluoromethoxy, $R^3$ represents cycloalkyl having 3 to 8 carbon atoms, or represents aryl having 6 to 10 carbon atoms, which is optionally monosubstituted to trisubstituted by identical or different substituents from the series comprising halogen or by straight-chain or branched alkyl having up to 8 carbon atoms, or represents straight-chain or branched alkyl having up to 10 carbon atoms, which is optionally substituted by a group of the formula —OR$^5$, in which $R^5$ has the abovementioned meaning, $R^4$ represents straight-chain or branched alkyl having up to 10 carbon atoms, or represents cycloalkyl, having 3 to 8 carbon atoms, X represents a group of the formula —CH$_2$—CH$_2$— or —CH=CH—, and R represents a group of the formula

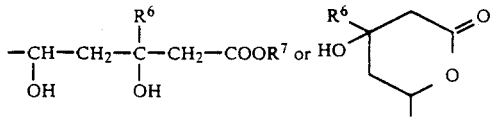

in which $R^6$ denotes hydrogen or straight-chain or branched alkyl having up to 10 carbon atoms and $R^7$ denotes hydrogen or straight-chain or branched alkyl having up to 10 carbon atoms, which may be substituted by phenyl, or denotes aryl having 6 to 10 carbon atoms or a cation, and their salts have now been found.

If $R^7$ forms an ester radical with the carboxyl group, a physiologically tolerable ester radical is preferably meant by this which is hydroly ed easily in vivo to give a free carboxyl group and as appropriate physiologically tolerable alcohol. These include, for example, alkyl esters (C$_1$ to C$_6$) and aralkyl esters (C$_7$ to C$_{10}$), preferably (C$_1$ to C$_4$)-alkyl esters and benzyl esters. Moreover, the following ester radicals may be mentioned: methyl esters, ethyl esters, propyl esters and benzyl esters.

If $R^7$ represents a cation, a physiologically tolerable metal or ammonium cation is preferably meant. Preferred cations in this connection are alkali metal or alkaline earth metal cations such as, for example, sodium, potassium, magnesium or calcium cations, and also aluminum or ammonium cations, and also non-toxic substituted ammonium cations from amines such as (C$_1$-C$_4$)dialkylamine, (C$_1$-C$_4$)-trialkylamine, procaine, dibenzylamine, N,N'-dibenzylethylenediamine, N-benzyl-β-phenylethylamine, N-methylmorpholine or N-ethylmorpholine, 1-ephenamine, dihydroabietylamine, N,N'-bis-dihydroabietylethylenediamine, N-loweralkylpiperidine and other amines which can be used for the formation of salts.

Surprisingly, the imino-substituted pyridines according to the invention show a superior inhibitory action of HMG-CoA reductase (3-hydroxy-3-methyl-glutarylcoenzyme A reductase).

Preferred compounds of the general formula (I) are those in which $R^1$ represents phenyl which is optionally monosubstituted or disubstituted by identical or different substituents from the series comprising fluorine, chlorine, bromine, hydroxyl, straight-chain or branched alkyl or alkoxy in each case having up to 6 carbon atoms or by phenoxy, $R^2$ represents phenyl which is optionally monosubstituted or disubstituted by identical or different substituents from the series comprising fluorine, chlorine, bromine or by straight-chain or branched alkyl having up to 6 carbon atoms, or represents straight-chain or branched alkyl having up to 8 carbon atoms, which is optionally substituted by phenyl or alkoxy having up to 6 carbon atoms, or represents a group of the formula —OR$^5$ in which $R^5$ denotes hydrogen or straight-chain or branched alkyl having up to 6 carbon atoms, which is optionally substituted by phenyl, or denotes phenyl which is optionally substituted by straight-chain or branched alkyl or alkoxy in each case having up to 6 carbon atoms, $R^3$ represents cyclopropyl, cyclobutyl, cyclopentyl or cyclohexyl, or represents phenyl which is optionally monosubstituted or disubstituted by identical or different substituents from the series comprising fluorine, chlorine, bromine or by straight-chain or branched alkyl having up to 6 carbon atoms, or represents straight-chain or branched alkyl having up to 8 carbon atoms, which is optionally substituted by a group of the formula —OR$^5$ in which R$^5$ has the abovementioned meaning, R$^4$ represents straight-chain or branched alkyl having up to 8 carbon atoms, or represents cyclopropyl, cyclopentyl or cyclohexyl, X represents a group of the formula —CH$_2$—CH$_2$— or —CH=CH—and R represents a group of the formula

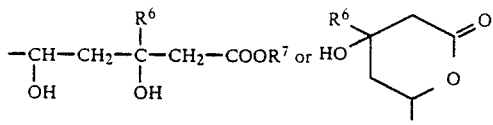

in which

R$^6$ denotes hydrogen or straight-chain or branched alkyl having up to 8 carbon atoms and R$^7$ denotes hydrogen or straight-chain or branched alkyl having up to 8 carbon atoms or benzyl, or denotes phenyl or a cation, and their salts.

Particularly preferred compounds of the general formula (I) are those in which R$^1$ represents phenyl which is optionally substituted by fluorine, chlorine, straight-chain or branched alkyl having up to 4 carbon atoms or phenoxy, or R$^2$ represents a group of the formula —OR$^5$ in which R$^5$ denotes hydrogen, benzyl or straight-chain or branched alkyl having up to 4 carbon atoms or denotes phenyl, R$^3$ represents cyclopropyl or phenyl, or represents a straight-chain or branched alkyl having up to 6 carbon atoms, which is optionally substituted by a group of the formula —OR$^5$ in which R$^5$ has the abovementioned meaning, R$^4$ represents straight-chain or branched alkyl having up to 6 carbon atoms or cyclopropyl, X represents a group —CH=CH—and R represents a group of the formula

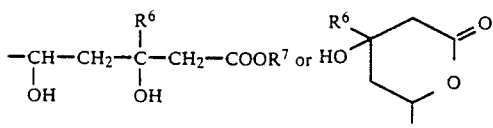

is which

R$^6$ denotes hydrogen, methyl, ethyl, propyl, isopropyl, butyl, isobutyl, or tert.butyl and R$^7$ denotes hydrogen, methyl, ethyl, propyl, isopropyl, butyl, isobutyl, tert.butyl or benzyl, or denotes a sodium, potassium, calcium, magnesium or ammonium ion, and their salts.

R$^6$ particularly preferably represents hydrogen.

The imino-substituted pyridines of the general formula (I) according to the invention have several asymmetrical carbon atoms and can therefore exist in various stereochemical forms. The invention relates to both the individual isomers and to their mixtures.

Depending on the meaning of the group X or the radical R, different stereoisomers are formed, which are illustrated in more detail in the following:

a) If the group —X— represents a group of the formula —CH=CH—, the compounds according to the invention can exist in two stereoisomeric forms which can have the E-configuration (II) or the Z-configuration (III) of the double bond:

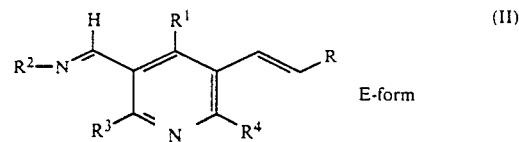

E-form

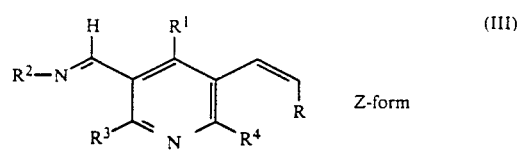

Z-form (R$^1$, R$^2$, R$^3$ and R$^4$ have the abovementioned meanings).

Preferred compounds of the general formula (I) are those which have the E-configuration (II).

b) If the radical —R represents a group of the formula

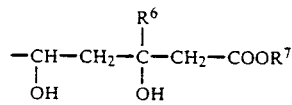

then the compounds of the general formula (I) have at least two asymmetric carbon atoms, namely the two carbon atoms to which the hydroxyl groups are bonded. Depending on the relative position of these hydroxyl groups to one another, the compounds according to the invention can be in the erythro-configuration (IV) or the threo-configuration (V).

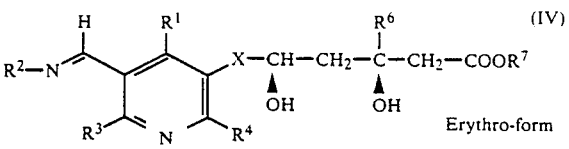

Erythro-form

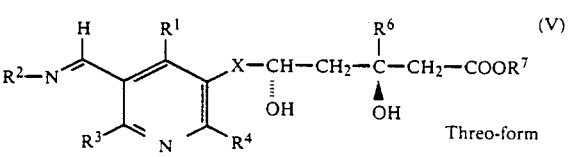

Threo-form

In each case, two enantiomers in turn exist of both the compounds in the erythro- and the threo-configuration, namely the 3R,5S-isomer or the 3S,5R-isomer (erythro form) and the 3R,5R-isomer and the 3S,5R-isomer (threo form).

The isomers in the erythro-configuration are preferred in this case, particularly preferably the 3R,5S-isomer and the 3R,5S-3S,5R-racemate.

c) If the radical —R represents a group of the formula

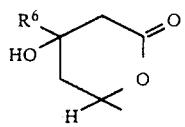

then the imino-substituted pyridines have at least two asymmetrical carbon atoms, namely the carbon atom to which the hydroxyl group is bonded, and the carbon atom to which the radical of the formula

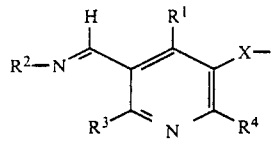

is bonded. Depending on the position of the hydroxyl group to the free valency on the lactone ring, the imino-substituted pyridines can be present as cis-lactones (VI) or as trans-lactones (VII).

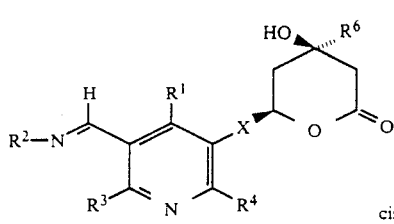

cis-lactone (VI)

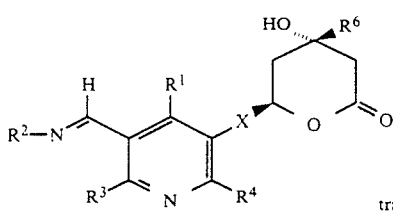

trans-lactone (VII)

In each case, two isomers in turn exist of both the cis-lactone and the trans-lactone, namely the 4R,6R-isomer or the 4S,6S-isomer (cis-lactone), and the 4R,6S-isomer or 4S,6R-isomer (trans-lactone). The trans-lactones are the preferred isomers. The 4R,6S-isomer (trans) and the 4R,6S-4S,6R-racemate is particularly preferred in this connection.

For example, the following isomeric forms of the imino-substituted pyridines may be mentioned:

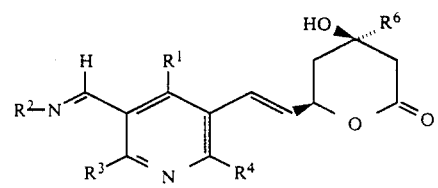

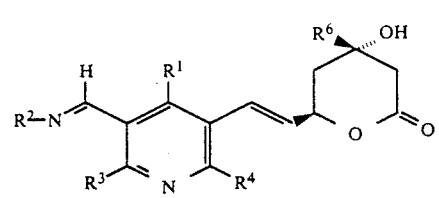

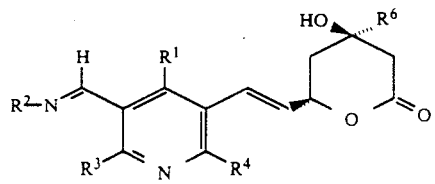

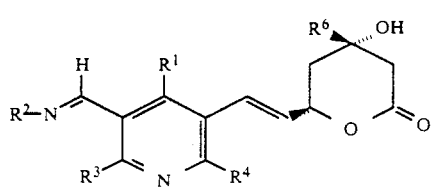

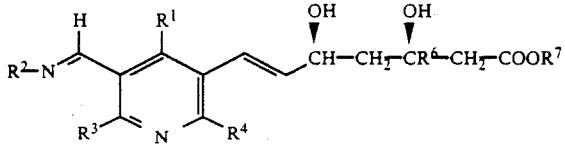

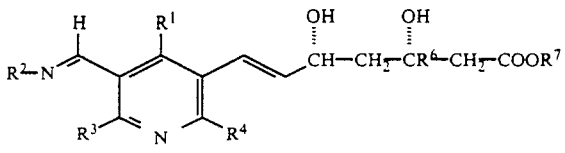

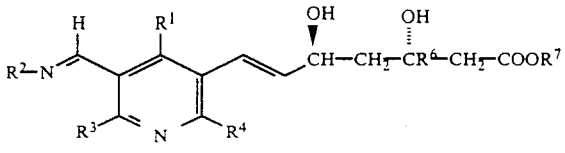

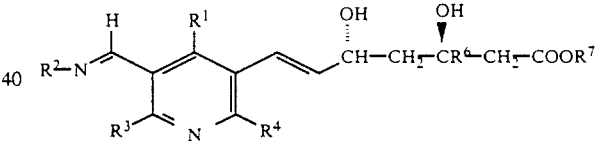

In addition, a process for the preparation of the imino-substituted pyridines of the general formula (I)

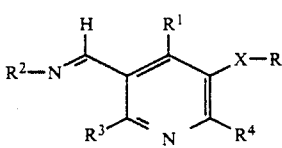

in which

R$^1$, R$^2$, R$^3$, R$^4$, X and R have the abovementioned meanings, has been found, which is characterized in that ketones of the general formula (VIII)

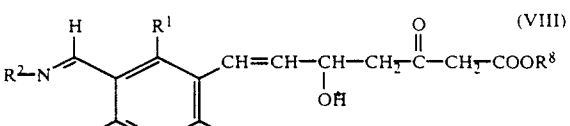

in which

R$^1$, R$^2$, R$^3$, R$^4$, X and R have the abovementioned meanings and

R[8] represents alkyl, are reduced, in the case of the preparation of the acids, the esters are hydrolyzed, in the case of the preparation of the lactones, the carboxylic acids are cyclized, in the case of the preparation of the salts, either the esters or the lactones are hydrolyzed, in the case of the preparation of the ethylene compounds (X=—CH$_2$CH$_2$—), the ethane compounds (X=—CH=CH—) are hydrogenated by customary methods, and, if appropriate, isomers are separated.

The process according to the invention can be illustrated by the following equation:

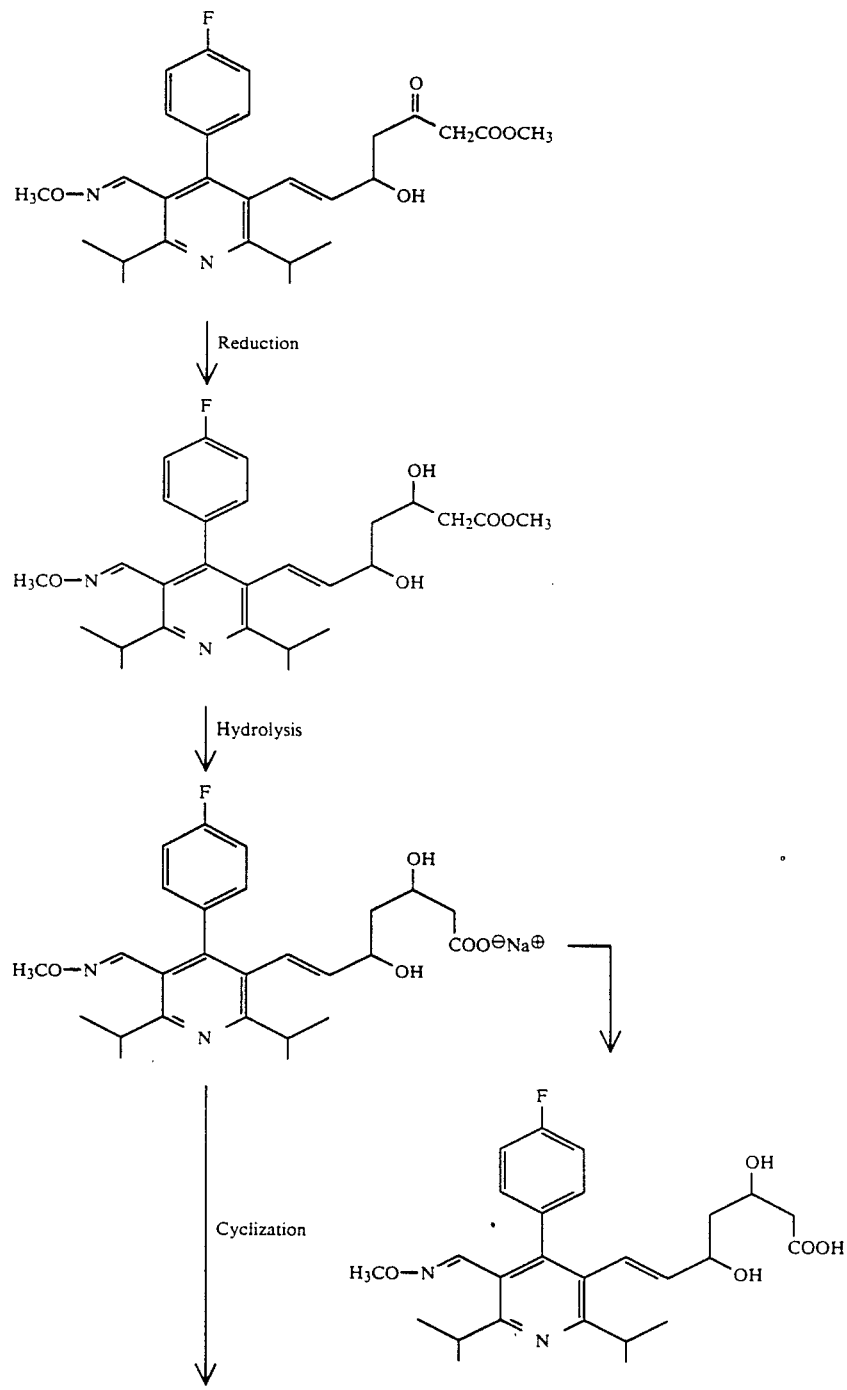

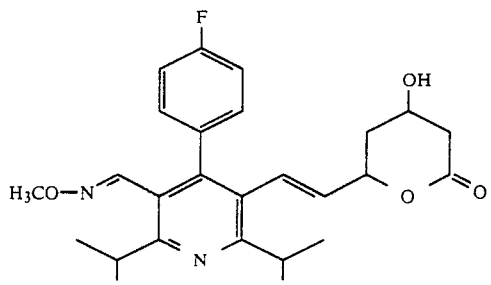

The reduction can be carried out using the customary reducing agents, preferably using those which are suitable for the reduction of ketones to hydroxyl compounds. In this case, reduction with metal hydrides or complex metal hydrides in inert solvents, if appropriate in the presence of a trialkylborane, is particularly suitable. Reduction is preferably carried out using complex metal hydrides such as, for example, lithium borohydride, sodium borohydride, potassium borohydride, zinc borohydride, lithium trialkylborohydrides, sodium trialkylborohydrides, sodium cyanoborohydrides or lithium aluminium hydride Very particularly preferably, reduction is carried out using sodium borohydride in the presence of triethylborane.

Suitable solvents in this connection are the customary organic solvents which do not change under the reaction conditions. These preferably include ethers such as, for example, diethyl ether, dioxane, tetrahydrofuran or dimethoxyethane, or halogenated hydrocarbons such as, for example, dichloromethane, trichloromethane, tetrachloromethane, 1,2-dichloroethane, or hydrocarbons such as, for example, benzene, toluene or xylene It is also possible to use mixtures of the solvents mentioned The reduction of the ketone group to the hydroxyl group is particularly preferably carried out under conditions in which the other functional groups such as, for example, the alkoxycarbonyl group, are not changed The use of sodium borohydride as a reducing agent, in the presence of triethylborane in inert solvents such as, preferably, ethers, is particularly suitable for this.

The reduction is in general carried out in a temperature range from −80° C. to +30° C., preferably from −78° C. to 0° C.

The reduction is in general carried out at normal pressure. However, it is also possible to carry out the process at reduced pressure or at elevated pressure (for example in a range from 0 5 to 5 bar).

In general, the reducing agent is employed in an amount of 1 to 2 moles, preferably 1 to 1.5 moles relative to 1 mole of the ketone compound.

Under the abovementioned reaction conditions, the carbonyl group is in general reduced to the hydroxyl group without reduction of the double bond to a single bond taking place In order to prepare compounds of the general formula (I) in which X represents an ethylene group, the reduction of the ketones (VIII) can be carried out under those conditions in which both the carbonyl group and the double bond are reduced Moreover, it is also possible to carry out the reduction of the carbonyl group and the reduction of the double bond in two separate steps The carboxylic acids in the context of the general formula (I) correspond to the formula (Ic)

(Ic)

in which
$R^1$, $R^2$, $R^3$, $R^4$, $R^6$ and X have the abovementioned meanings, The carboxylic acid esters in the context of the general formula (I) correspond to the formula (Id)

(Id)

in which
$R^1$, $R^2$, $R^3$, $R^4$, $R^6$, $R^8$ and X have the abovementioned meanings.

The salts of the compounds according to the invention in the context of the general formula (I) correspond to the formula (Ie)

(Ie)

in which
$R^1$, $R^2$, $R^3$, $R^4$, $R^5$, $R^6$, $R^8$ and X have the abovementioned meanings.

The salts of the compounds according to the invention in the context of the general formula (I) correspond to the formula (Ie)

(Ie)

in which
$R^1$, $R^2$, $R^3$, $R^4$, $R^6$ and X have the abovementioned meanings, and $M^{n+}$ represents a cation, where n indicates the valency.

The lactones in the context of the general formula (I) correspond to the formula (If)

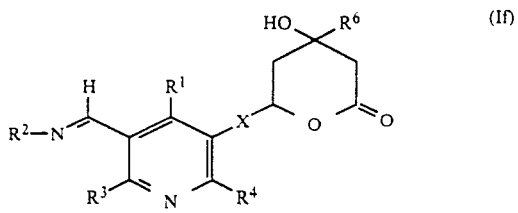

in which $R^1$, $R^2$, $R^3$, $R^4$, $R^6$ and X have the abovementioned meanings.

In order to prepare the carboxylic acids of the general formula (Ic) according to the invention, the carboxylic esters of the general formula (Id) or the lactones of the general formula (If) are in general hydrolyzed by customary methods. The hydrolysis is in general carried out by treating the esters or the lactones with customary bases in inert solvents, the salts of the general formula (Ie) in general being formed first, and it then being possible to convert these into the free acids of the general formula (Ic) in a second step by treating with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert.butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to use mixtures of the solvents mentioned.

The hydrolysis is in general carried out in a temperature range of 0° C. to +100° C., preferably +20° C. to 80° C.

In general, the hydrolysis is carried out at normal pressure However, it is also possible to work at reduced pressure or at elevated pressure (for example from 0.5 to 5 bar).

When carrying out the hydrolysis, the base is in general employed in an amount of 1 to 3 moles, preferably 1 to 1.5 moles, relative to 1 mole of the ester or the lactone. Molar amounts of the reactants are particularly preferably used.

When carrying out the hydrolysis, the salts of the compounds (Ie) according to the invention are formed in the first step as intermediates which can be isolated. The acids (Ic) according to the invention are obtained by treating the salts (Ie) with customary inorganic acids. These preferably include mineral acids such as, for example, hydrochloric acid, hydrobromic acid, sulphuric acid or phosphoric acid. In this case, it has proved advantageous in the preparation of the carboxylic acids (Ic) to acidify the basic reaction mixture from the hydrolysis in a second step without isolation of the salts. The acids can then be isolated in a customary manner.

In order to prepare the lactones of the formula (If) according to the invention, the carboxylic acids (Ic) according to the invention are in general cyclized by customary methods, for example by heating the corresponding acid in inert organic solvents, if appropriate in the presence of molecular sieve.

Suitable solvents for the cyclization are hydrocarbons such as benzene, toluene, xylene, mineral oil fractions, or tetralin or diglyme or triglyme. Benzene, toluene or xylene are preferably employed. It is also possible to employ mixtures of the solvents mentioned. Particularly preferably, hydrocarbons, in particular toluene, are used in the presence of molecular sieve.

The cyclization is in general carried out in a temperature range of −40° C. to +200° C., preferably −25° C. to +50° C.

The cyclization is in general carried out at normal pressure, but it is also possible to carry out the process at reduced pressure or at elevated pressure (for example in a range from 0.5 to 5 bar).

Moreover, the cyclization is also carried out in inert organic solvents, with the aid of cyclizing or dehydrating agents. Dehydrating agents used in this connection are preferably carbodiimides. Carbodiimides employed are preferably N,N'-dicyclohexylcarbodiimide paratoluenesulphonate, N-cyclohexyl-N'-[2-(N''-methylmorpholinium)ethyl]carbodiimide or N-(3-dimethylaminopropyl)-N'-ethylcarbodiimide hydrochloride.

Suitable solvents in this connection are the customary organic solvents These preferably include ethers such as diethyl ether, tetrahydrofuran or dioxane, or chlorinated hydrocarbons such as methylene chloride, chloroform or carbon tetrachloride, or hydrocarbons such as benzene, toluene, xylene or mineral oil fractions Chlorinated hydrocarbons such as, for example, methylene chloride, chloroform or carbon tetrachloride, or hydrocarbons such as benzene, toluene, xylene, or mineral oil fractions are particularly preferred. Chlorinated hydrocarbons such as, for example, methylene chloride, chloroform or carbon tetrachloride are very particularly preferably employed.

The cyclization is in general carried out in a temperature range of 0° C. to +80° C., preferably +10° C. to 50° C.

When carrying out the cyclization, it has proved advantageous to employ the cyclization methods using carbodiimides as dehydrating agents.

The separation of the isomers into the stereoisomerically uniform constituents is in general carried out by customary methods such as are described, for example, by E. L. Eliel, Stereochemistry of Carbon Compounds, McGraw Hill, 1962. The separation of the isomers in the racemic ester step is preferred in this connection. Particularly preferably, the racemic mixture of the trans lactones (VII) is in this case converted by treating either with D-(+)- or L-(−)-α-methylbenzylamine by customary methods into the diastereomeric dihydroxyamides (Ig)

(Ig)

The separation of isomers is intended to be illustrated by way of example in the following scheme:

invention in enantiomerically pure form that the configuration of the final products according to the method described above is dependent on the configuration of the starting materials.

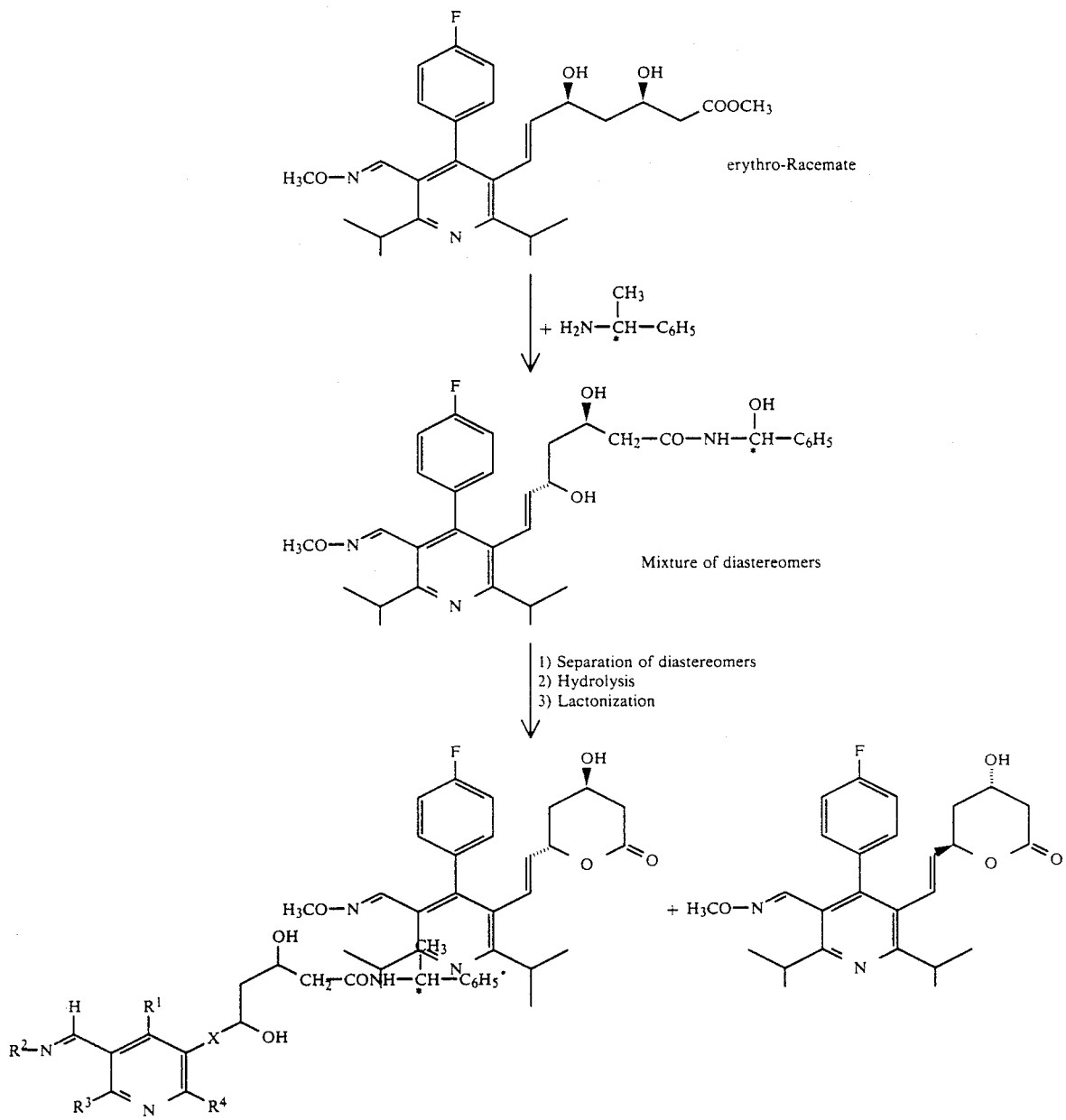

which can subsequently be separated, as is customary, into the individual diastereomers by chromatography or crystallization. Subsequent hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, gives the corresponding enantiomerically pure dihydroxy acids (Ic), which can be converted into the enantiomerically pure lactones by cyclization as described above. In general, it holds true for the preparation of the compounds of the general formula (I) according to the The ketones (VIII) employed as starting materials are new.

A process for the preparation of the ketones of the general formula (VIII) according to the invention

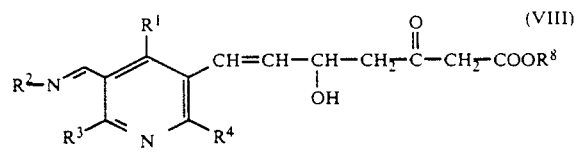

$R^1$, $R^2$, $R^3$ and $R^8$ have the abovementioned meanings, has been found, which is characterized in that aldehydes of the general formula (IX)

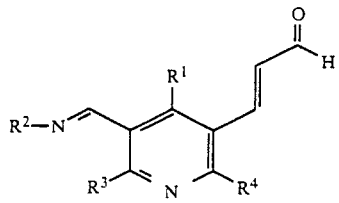

in which $R^1$, $R^2$, $R^3$ and $R^4$ have the abovementioned meanings, are reacted in inert solvents with acetoacetic acid esters of the general formula (X)

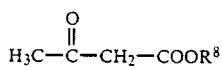

in which $R^8$ has the abovementioned meaning, in the presence of bases.

The process according to the invention can be illustrated, for example, by the following equation:

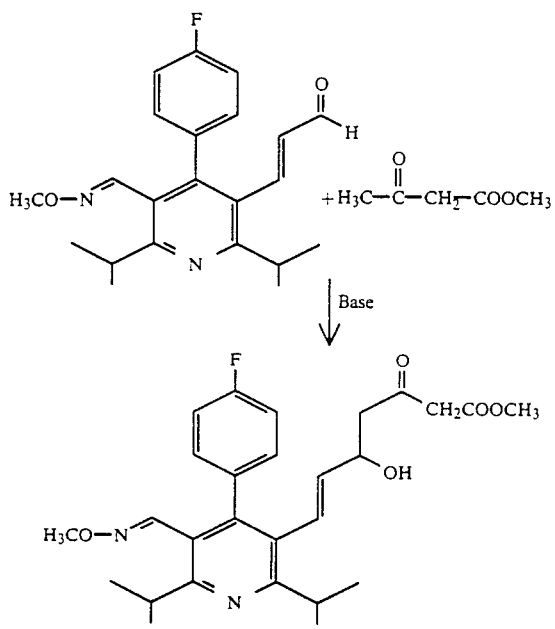

Suitable bases in this connection are the customary strongly basic compounds. These preferably include organolithium compounds such as, for example, n-butyllithium, sec.butyllithium, tert.butyllithium or phenyllithium, or amides, such as, for example, lithium diisopropylamide, sodium amide or potassium amide, or lithium hexamethyldisilylamide, or alkali metal hydrides such as sodium hydride or potassium hydride It is also possible to employ mixtures of the bases mentioned. n-Butyllithium or sodium hydride or a mixture thereof is particularly preferably employed Additions of metal halides, such as, for example, magnesium chloride, zinc chloride or zinc bromide may be advantageous. The addition of zinc halides is particularly preferable.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is also possible to employ mixtures of the solvents mentioned. Ethers such as diethyl ether or tetrahydrofuran are particularly preferably used.

The reaction is in general carried out in a temperature range of $-80°$ C. to $+50°$ C., preferably $-20°$ C. to room temperature.

The process is in general carried out at normal pressure, but it is also possible to carry out the process at reduced pressure or at elevated pressure, for example in a range from 0.5 to 5 bar.

When carrying out the process, the acetoacetic acid ester is in general employed in an amount of 1 to 2, preferably 1 to 1.5 moles, relative to 1 mole of the aldehyde.

The acetoacetic acid esters of the formula (X) employed as starting materials are known or can be prepared by known methods [Beilstein's Handbuch der organischen Chemie (Beilstein's Handbook of Organic Chemistry) III, 632; 438].

Examples of acetoacetic acid esters which may be mentioned for the process according to the invention are: methyl acetoacetate, ethyl acetoacetate, propyl acetoacetate and isopropyl acetoacetate.

The preparation of the aldehydes of the general formula (IX) employed as starting materials is intended to be illustrated by way of example in the following scheme [A].

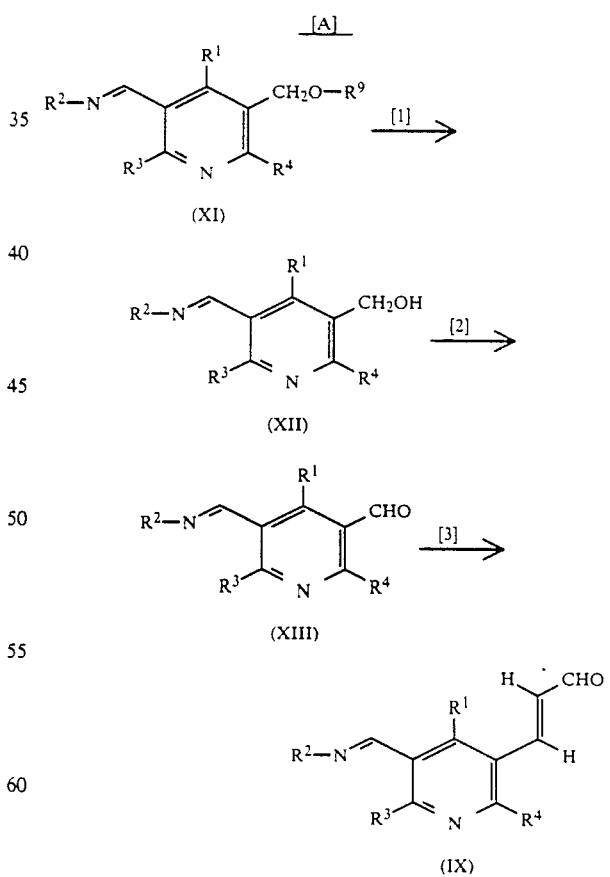

In this connection, the imino-substituted pyridines of the formula (XI), in which $R^9$ represents a typical hydroxyl protecting group, for example the tert.butyl-dimethylsilyl radical, are converted into the hydroxymethyl compounds (XII) in the first step [1] in inert solvents such as ether, for example diethyl ether, tetrahydrofuran or dioxane, preferably tetrahydrofuran, with removal of the radical $R^9$ by a customary method, for example using tetrabutylammonium fluoride. The reaction proceeds in a temperature range of $-10°$ C. to $+60°$ C., preferably at $0°$ C. to $+30°$ C.

The hydroxymethyl compounds (XII) are oxidized to the aldehydes (XIII) by customary methods in the second step [2]. The oxidation can be carried out, for example, using pyridinium chlorochromate, if appropriate in the presence of alumina, in inert solvents such as chlorinated hydrocarbons, preferably methylene chloride, in a temperature range of $0°$ C. to $60°$ C., preferably at room temperature, or else using trifluoroacetic acid/dimethyl sulphoxide according to the customary methods of the Swern oxidation. The aldehydes (XIII) are reacted to give the aldehydes (IX) in the third step [3] using diethyl 2-(cyclohexylamino)-vinylphosphonate in the presence of sodium hydride in inert solvents such as ethers, for example diethyl ether, tetrahydrofuran or dioxane, preferably in tetrahydrofuran, in a temperature range of $-20°$ C. to $+40°$ C., preferably $-5°$ C. to room temperature.

The substituted pyridines of the formula (XI) employed as starting materials are new. They are obtained in general according to scheme [B], by a process in which

[B] Compounds of the general formula (XIV)

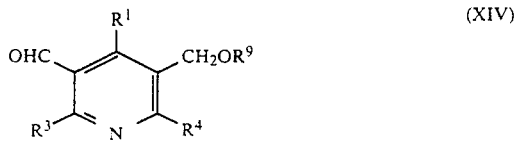

in which $R^1$, $R^3$, $R^4$ and $R^9$ have the abovementioned meanings, are reacted with amines or hydroxylamine derivatives of the general formula (XV)

in which $R^2$ has the abovementioned meaning, in one of the abovementioned solvents, preferably methylene chloride, in a temperature range of $0°$ C. to $+70°$ C., preferably at room temperature.

The compounds of the general formula (XIV) are known per se or can be prepared by a known method (compare DOS 3,801,406).

The compounds of the general formula (XV) are also known (compare Beilstein 1, 288, Houben-Weyl's "Methoden der organischen Chemie" (Methods of Organic Chemistry), vol. XII 1 and XII 2).

The compounds of the general formula (I) according to the invention have useful pharmacological properties and can be employed in medicaments. In particular, they are inhibitors of 3-hydroxy-3-methylglutaryl-coenzyme A (HMG-CoA) reductase and, as a result, inhibitors of cholesterol biosynthesis. They can therefore be employed for the treatment of hyperlipoproteinaemia, lipoproteinaemia atherosclerosis. The active compounds according to the invention additionally cause a lowering of the cholesterol content in the blood.

The enzyme activity determination was carried out as modified by G. C. Ness et al., Archives of Biochemistry and Biophysics 197, 493-499 (1979). Male Rico rats (body weight 300-400 g) were treated with altromin powdered feed, to which 40 g of cholestyramine/kg of feed had been added, for 11 days After decapitation, the livers were removed from the animals and placed on ice. The livers were comminuted and homogenized three times in a Potter-Elvejem homogenizer in 3 volumes of 0.1 M sucrose, 0.05 M KCl, 0.04 M $K_xH_y$ phosphate, 0.03 M ethylenediaminetetraacetic acid, 0.002 M dithiothreitol (SPE) buffer pH 7.2. The mixture was then centrifuged at 5,000 g for 15 minutes and the sediment was discarded. The supernatant was sedimented at 100,000 g for 75 minutes. The pellet is taken up in $\frac{1}{4}$ volume of SPE buffer, homogenized again and then centrifuged again at 100,000 g for 60 minutes The pellet is taken up using a 5-fold amount of its volume of SPE buffer, homogenized and frozen and stored at $-78°$ C. (=enzyme solution).

For testing, the test compounds (or mevinolin as a reference substance) were dissolved in dimethylformamide with the addition of 5 vol -% of 1 N NaOH and employed in the enzyme test using 10 $\mu$l in various concentrations. The test was begun after 20 minutes preincubation of the compounds with the enzyme at $37°$ C. The test mixture amounted to 0.380 ml and contained 4 $\mu$mol of glucose 6-phosphate, 1.1 mg of bovine serum albumin, 2.1 $\mu$mol of dithiothreitol, 0.35 $\mu$mol of NADP, 1 unit of glucose 6-phosphate dehydrogenase, 35 $\mu$mol of $K_xH_y$ phosphate pH 7.2, 20 $\mu$l of enzyme preparation and 56 nmol of 3-hydroxy-3-methyl-glutaryl coenzyme A (glutaryl3-$^{14}$C) of 100,000 dpm.

After an incubation of 60 minutes at $37°$ C., the mixture was centrifuged and 600 $\mu$l of the supernatant was applied to a $0.7 \times 4$ cm column packed with a 5-chloride 100-200 mesh (anion exchanger). The column was washed with 2 ml of distilled water and 3 ml of Aquasol was added to the running plus washing water and counted in an LKB scintillation counter. $IC_{50}$ values were determined by intrapolation by plotting the percentage inhibition against the concentration of the compound in the test. In order to determine the relative inhibitory potency, the $IC_{50}$ value of the reference substance mevinolin was set at 1 and compared with the simultaneously determined $IC_{50}$ value of the test compound.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 98% by weight, preferably 1 to 90% by weight, of the total mixture, i.e. in amounts which are sufficient in order to achieve the dosage range indicated.

The formulations are prepared, for example, by extending the active compounds with solvents and/or excipients, if appropriate using emulsifiers and/or dispersants, it being possible, for example, in the case of the use of water as a diluent, to use, if appropriate, organic solvents as auxiliary solvents.

Examples of auxiliary solvents which may be mentioned are: water, non-toxic organic solvents, such as paraffins (for example mineral oil fractions), vegetable oils (for example ground nut/sesame oil), alcohols (for example: ethylalcohol, glycerol), excipients, such as, for example, ground natural minerals (for example, kaolins, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersing agents (for example lignin-sulphite waste liquors, methylcellulose, starch and polyvinylpyrrolidone) and lubricants (for example magnesium stearate, talc, stearic acid and sodium laurylsulphate).

Administration is carried out in a customary manner, preferably orally, parenterally, perlingually or intravenously. In the case of oral administration, tablets can of course also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium laurylsulphate and talc can additionally be used for tabletting. In the case of aqueous suspensions, various flavor enhancers or colorants may be added to the active compounds in addition to the abovementioned auxiliaries.

In the case of parenteral administration, solutions of the active compounds can be employed using suitable liquid excipient materials.

In general, it has proved advantageous on intravenous administration to administer amounts of about 0.001 to 1 mg/kg, preferably about 0.01 to 0.5 mg/kg of body weight to attain effective results, on oral administration the dosage is about 0.01 to 20 mg/kg, preferably 0.1 to 10 mg/kg of body weight.

In spite of this it may be necessary to deviate from the amounts mentioned, depending in particular on the body weight or the manner of administration, on individual behavior towards the medicament, the manner of its formulation and the point in time or interval at which administration takes place.

Thus, in some cases it may be sufficient to manage with less than the minimum amount previously mentioned, while in other cases the upper limit mentioned must be exceeded. In the case of the administration of relatively large amounts, it may be advisable to divide these into a number of individual doses over the course of the day.

STARTING COMPOUNDS

Example I (E/Z)-4-carboxyethyl-5-(4-fluorophenyl)-2-methyl-pent-4en-3-one

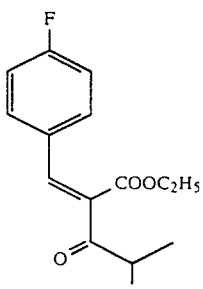

62 g (0.5 mol) of 4-fluorobenzaldehyde and 79 g (0.5 mol) of ethyl isobutyrylacetate are initially introduced into 300 ml of isopropanol and a mixture of 2.81 ml (28 mmol) of piperidine and 1.66 ml (29 mmol) of acetic acid in 40 ml of isopropanol is added. The mixture is stirred at room temperature for 48 hours, concentrated in vacuo and the residue is distilled in a high vacuum.

B.p. 0.5 mm; 127° C.

Yield: 108.7 g (82.3% of theory)

Example II

Diethyl 1,4-dihydro-2,6-diisopropyl-4-(4-fluorophenyl)pyridine-3,5-dicarboxylate

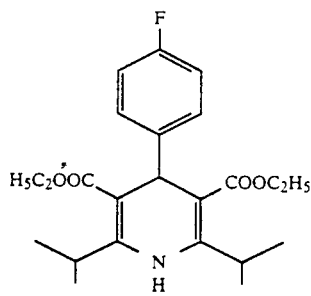

98 g (0.371 mol) of the compound from Example I are heated to reflux for 18 h with 58.3 g (0.371 mol) of ethyl 3-amino-4-methyl-pent-2-enoate in 300 ml of ethanol. The mixture is cooled to room temperature, the solvent is evaporated in vacuo and the unreacted starting materials are removed by distillation in a high vacuum at 130° C. The remaining syrup is stirred with n-hexane and the deposited precipitate is filtered off with suction, washed with n-hexane and dried in a desiccator.

Yield: 35 g (23.4% of theory)

$^1$H NMR (CDCl$_3$): δ=1.1–1.3 (m, 18H); 4.05–4.25 (m, 6H); 5.0 (s, 1H); 6.13 (s, 1H); 6.88 (m, 2H); 7.2 (m, 2H) ppm.

Example III

Diethyl 2,6-diisopropyl-4-(4-fluorophenyl)-pyridine-3,5-dicarboxylate

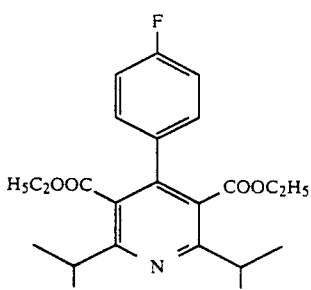

3.8 g (16.4 mmol) of 2,3-dichloro-5,6-dicyano-p-benzoquinone are added to a solution of 6.6 g (16.4 mmol) of the compound from Example II in 200 ml of methylene chloride p.A. and the mixture is stirred at room temperature for 1 hour. It is then filtered through kieselguhr with suction, and the methylene chloride phase is extracted 3 times with 100 ml of water each time and dried over magnesium sulphate. After concentrating in vacuo, the residue is chromatographed on a column (100 g of silica gel 70–230 mesh, φ 3.5 cm, using ethyl acetate/ petroleum ether 1:9)

Yield: 5.8 g (87.9% of theory)

$^1$H NMR (CDCl$_3$): δ=0.98 (t, 6H); 1.41 (d, 12H); 3.1 (m, 2H); 4.11 (q, 4H); 7.04 (m, 2H); 7.25 (m, 2H) ppm.

Example IV

Ethyl 2,6-diisopropyl-4-(4-fluorophenyl)-5-hydroxymethyl-pyridine-3-carboxylate

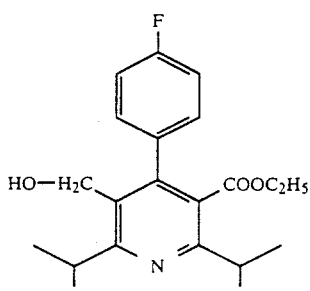

21 ml (80.5 mmol) of a 3.5 molar solution of sodium bis-(2-methoxy ethoxy)-dihydroaluminate in toluene are added at −10° C. to −5° C. under nitrogen to a solution of 9.2 g (23 mmol) of the compound from Example III in 100 ml of dry tetrahydrofuran and the mixture is stirred at room temperature for 5 h. After cooling to 0° C., 100 ml of water are cautiously added dropwise and the mixture is extracted 3 times with 100 ml of ethyl acetate each time. The combined organic phases are washed with saturated sodium chloride solution, dried over magnesium sulphate and concentrated in vacuo. The residue is chromatographed on a column (200 g of silica gel 70–230 mesh, φ 4.5 cm, using ethyl acetate/petroleum ether 3:7).

Yield: 7.2 g (87.2% of theory)

1H NMR (CDCl$_3$):δ=0.95 (t, 3H); 1.31 (m, 12H); 3.05 (m, 1H); 3.48 (m, 1H), 3.95 (q, 2H); 4.93 (d, 2H); 7.05–7.31 (m, 4H) ppm.

Example V

Ethyl 5-(tert.butyldimethylsilyloxymethyl)-2,6-diisopropyl-4-(4-fluorophenyl)-pyridine-3-carboxylate

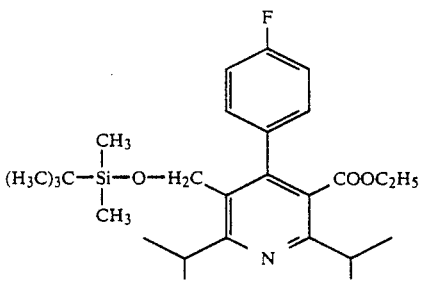

2.1 g (13.8 mmol) of tert.butyldimethylsilyl chloride, 1.8 g (27.5 mmol) of imidazole and 0.05 g of 4-dimethylaminopyridine are added at room temperature to a solution of 4.5 g (12.5 mmol) of the compound from Example IV in 50 ml of dimethylformamide. The mixture is stirred overnight at room temperature, 200 ml of water are added and it is adjusted to pH 3 with 1 N hydrochloric acid. The mixture is extracted three times with 100 ml of ether each time, and the combined organic phases are washed once with saturated sodium chloride solution, dried over magnesium sulphate and concentrated in vacuo. The residue is chromatographed on a column (150 g of silica gel, 70–230 mesh, φ 4 cm, using ethyl acetate/petroleum ether 1:9).

Yield: 4.2 g (73.7% of theory)

$^1$H NMR (CDCl$_3$): δ=0.0 (s, 6H); 0.9 (s, 9H); 1.02 (t, 3H); 1.35 (m, 12H); 3.1 (m, 1H); 3.47 (m, 1H); 4.03 (q, 2H); 4.4 (s, 2H); 7.05–7.40 (m, 4H) ppm.

Example VI 3-(tert.Butyldimethylsilyloxymethyl)-2,6-diisopropyl-4-(4-fluorophenyl)-5-hydroxymethyl-pyridine

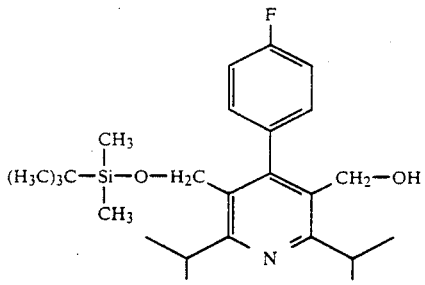

9.2 ml (32.2 mmol) of a 3.5 molar solution of sodium bis-(2-methoxyethoxy)-dihydroaluminate in toluene are added at 0° C. under nitrogen to a solution of 4.2 g (9.2 mmol) of the compound from Example V in 100 ml of dry tetrahydrofuran and the mixture is stirred overnight at room temperature. After cooling to 0° C., 100 ml of water are cautiously added dropwise and the mixture is extracted 3 times with 100 ml of ethyl acetate each time. The combined organic phases are washed once with saturated sodium chloride solution, dried over magnesium sulphate and concentrated in vacuo. The residue is chromatographed on a column (100 g of silica gel 70–230 mesh, φ 3.5 cm, using ethyl acetate/petroleum ether 2:8). Yield: 2.4 g (60% of theory)

$^1$H NMR (CDCl$_3$): δ=0.2 (s, 6H); 1.11 (s, 9H); 1.6 (m, 12H); 3.7 (m, 2H); 4.55 (s, 2H); 4.65 (d, 2H); 7.35–7.55 (m, 4H) ppm.

Example VII 5-(tert.Butyldimethylsilyloxymethyl)-2,6-diisopropyl-4-(4-fluorophenyl)-pyridine-3-carbaldehyde

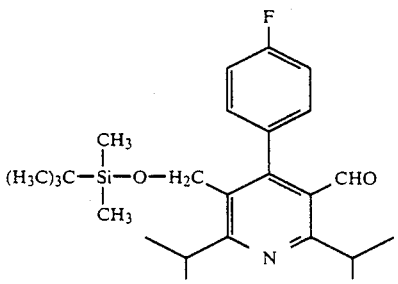

1 24 g (12.4 mmol) of neutral alumina and 2.7 g (12.4 mmol) of pyridinium chlorochromate are added to a solution of 2.7 g (6.2 mmol) of the compound from Example VI in 50 ml of methylene chloride and the mixture is stirred at room temperature for 1 hour. The solution is filtered with suction through kieselguhr, which is then washed with 200 ml of methylene chloride. The methylene chloride phase is concentrated in vacuo and the residue is chromatographed on a column (100 g of silica gel 70–230 mesh, φ 3.5 cm, using ethyl acetate/petroleum ether 1:9).

Yield: 2 g (77% of theory)

$^1$H NMR (CDCl$_3$): δ=0.0 (s, 6H); 0.9 (s, 9H); 1.35 (m, 12H); 3.5 (m, 1H); 3.9 (m, 1H); 4.38 (s, 2H); 7.15–7.35 (m, 4H); 9.8 (s, 1H) ppm.

PREPARATION EXAMPLES

Example 1

3-(tert.-Butyldimethylsilyloxymethyl)-2,6-diisopropyl-4-(4-fluorophenyl)5-methoxyiminomethyl-pyridine

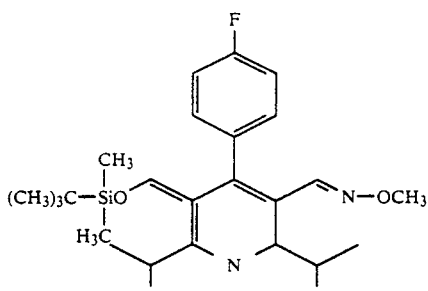

626 mg (7.5 mmol) of 0-methylhydroxylamine hydrochloride and 0.6 ml (7.5 mmol) of pyridine are added to a solution of 2.1 g (5 mmol) of the compound from Example VII in 50 ml of ethanol p.A. and the mixture is heated under reflux for 1 hour. After cooling to room temperature, it is concentrated to one half on a rotary evaporator. The crystals which deposit on further cooling to 0° C. are filtered off with suction and dried.

Yield: 1.52 g (66.4 % of theory)

$^1$H NMR (CDCl$_3$): δ=0.01 (s, 6H); 0.91 (s, 9H); 1.48 (m, 2H); 3.50 (sept. 1H); 3.68 (sept. 1H); 3.89 (s, 3H); 4.39 (s, 2H); 7.10–7.30 (m, 4H); 7.82 (s, 1H) ppm.

Example 2

2,6-Diisopropyl-4-(4-fluorophenyl)-3-hydroxymethyl-5-methoxyiminomethyl-pyridine

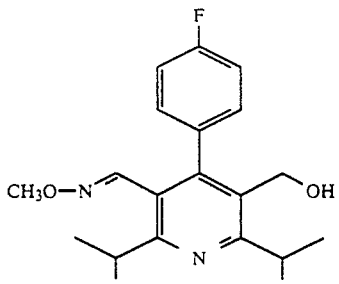

3.3 ml (3.3 mmol) of 1 M tetrabutylammonium fluoride solution in tetrahydrofuran is added to a solution of 1.5 g (3.3 mmol) of the compound from Example 1 in 15 ml of absolute tetrahydrofuran and the mixture is stirred at room temperature for 1 hour. Saturated sodium hydrogencarbonate solution is then added to the reaction solution and it is extracted several times with methylene chloride. The combined organic phases are dried (MgSO$_4$), concentrated and then filtered through silica gel.

Yield: 1.07 g of crude product (94.3% of theory)

$^1$H NMR (CDCl$_3$): δ1.22 (d, 3H); 1.27 (d, 3H); 3.38 (sept., 1H); 3.48 (sept., 1H); 3.72 (s, 3H); 4.33 (d, 2H) 7.0–7.2 (m, 4H); 7.65 (s, 1H) ppm.

Example 3

2,6-Diisopropyl-4-(4-fluorophenyl)-5-methoxyiminomethylpyridine-3-carbaldehyde

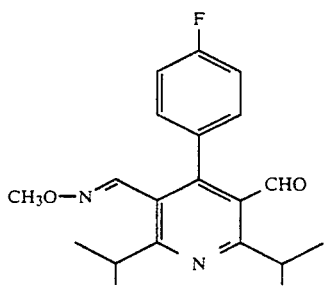

0.62 g (6.2 mmol) of neutral alumina and 1.3 g (6.1 mmol) of pyridinium chlorochromate are added to a solution of 1.05 g (3.05 mmol) of the compound from Example 2 in 50 ml of methylene chloride and the mixture is stirred at room temperature for 1 hour. It is filtered through kieselguhr and then washed with 200 ml of methylene chloride. The methylene chloride phase is concentrated in vacuo and the residue is chromatographed on a column (100 g of silica gel, 70–230 mesh, diameter 3.5 cm) using ethyl acetate/petroleum ether 1:9.

Yield: 830 mg (79.6% of theory)

$^1$H NMR (CDCl$_3$): δ=1.32 (d, 6H); 3.63 (sept., 1H); 3.84 (sept., 1H); 3.86 (s, 3H); 7.1–7.3 (m, 4H); 7.78 (s, 1H), 9.79 (s, 1H) ppm.

Example 4

(E)-3-[2,6-diisopropyl-4-(4-fluorophenyl)-5-methoxyrminomethyl-pyrid-3-yl]-prop-2-enal

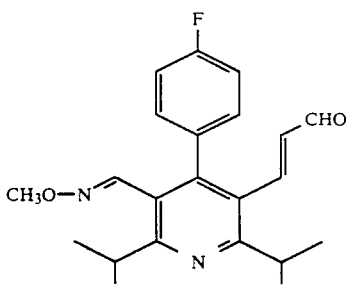

750 mg (2.9 mmol) of diethyl 2-(cyclohexylamino)-vinylphosphonate, dissolved in 30 ml of dried tetrahydrofuran, are added dropwise at −5° C. under nitrogen to a suspension of 110 mg (3.6 mmol) of 80% pure sodium hydride in 15 ml of dry tetrahydrofuran. After 30 minutes, 810 mg (2.4 mmol) of the compound from Example 3 in 40 ml of dry tetrahydrofuran are added dropwise at the same temperature and the mixture is heated to reflux for 30 minutes. After cooling to room temperature, the mixture is added to 200 ml of ice-cold water and extracted three with 100 ml of ethyl acetate each time. The combined organic phases are washed with saturated sodium chloride solution and dried over magnesium sulphate. After concentrating in vacuo, the residue is taken up in 70 ml of toluene, a solution of 4.5 g (3.5 mmol) of oxalic acid dihydrate in 30 ml of water is added and the mixture is heated to reflux for 30 minutes.

After cooling to room temperature, the phases are separated, and the organic phase is washed with saturated sodium chloride solution, dried over magnesium sulphate and concentrated in vacuo. The residue is chromatographed on a column (100 g of silica gel, 70–230 mesh, diameter 3.5 cm) using ethyl acetate/petroleum ether 1:9.

Yield: 430 mg (48.7% of theory)

$^1$H NMR (CDCl$_3$): δ=1.32 (d, 6H); 3.32 (sept., 1H); 3.61 (sept., 1H); 3.83 (s, 3H); 6.03 (dd, 1H); 7.0–7.2 (m, 4H); 7.28 (d, 1H); 7.77 (s, 1H) ppm.

Example 5

Methyl (E)-7-[2,6-diisopropyl-4-(4-fluorophenyl)-5-methoxyiminomethyl-pyrid-3-yl]-5-hydroxy-3-oxo-hept-6-enoate

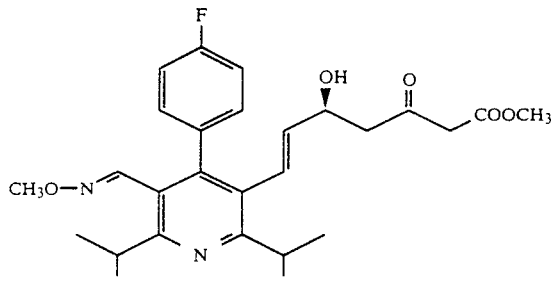

0.18 ml (1.65 mmol) of methyl acetoacetate in 5 ml of dry tetrahydrofuran are added dropwise at −5° C. under nitrogen to a suspension of 67 mg (2.2 mmol) of 80% pure sodium hydride in 10 ml of dry tetrahydrofuran. After 15 min, 1.01 ml (1.65 mmol) of 15% strength butyllithium in n-hexane are added dropwise at the same temperature and the mixture is then stirred for 15 minutes. 410 mg (1.1 mmol) of the compound from Example 4, dissolved in 10 ml of dry tetrahydrofuran, are then added and the mixture is stirred at −5° C. for 30 minutes. 0.3 ml of glacial acetic acid is cautiously added to the reaction solution, it is diluted with 100 ml of water and the mixture is extracted 3 times with 100 ml of ether each time. The combined organic phases are washed twice with saturated sodium hydrogencarbonate solution, dried over magnesium sulphate and concentrated in vacuo. The residue is filtered through silica gel (solvent: ethyl acetate/ petroleum ether 1:1).

Yield: 490 mg (91.6% of theory)

$^1$H NMR (CDCl$_3$): δ=1.25 (m, 6H); 2.47 (m, 2H); 3.29 (sept., 1H); 3.42 (s, 2H); 3.58 (sept., 1H); 3.75 (s, 3H); 3.82 (s, 3H); 4.51 (m, 1H) 5.38 (dd, 1H); 6.36 (d, 1H); 7.0−7.2 (m, 4H); 7.77 (s, 1H) ppm.

Example 6

Methyl erythro-(E)-7-[2,6-diisopropyl-4-(4-fluorophenyl)5-methoxyiminomethyl-pyrid-3-yl]-3,5-dihydroxy-hept-6-enoate

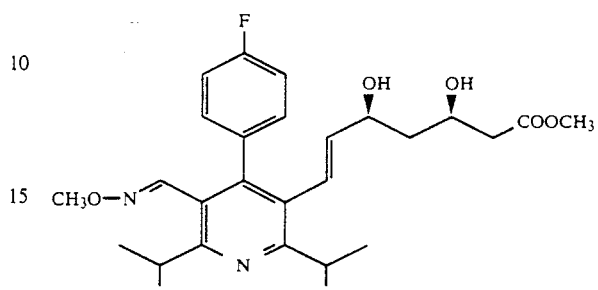

1.2 ml (1.2 mmol) of 1 M triethylborane solution in tetrahydrofuran are added at room temperature to a solution of 470 mg (1 mmol) of the compound from Example 5 in 10 ml of dry tetrahydrofuran, air is passed through the solution for 5 minutes and the mixture is cooled to an internal temperature of −30° C. 46 mg (1.2 mmol) of sodium borohydride and, slowly, 0.8 ml of methanol are added, the mixture is stirred at −30° C. for 30 minutes and a mixture of 3 ml of 30% strength hydrogen peroxide and 10 ml of water is then added. The temperature is allowed to rise to 0° C. during the course of this and the mixture is then stirred for a further 30 minutes. The mixture is extracted three times with 70 ml of ethyl acetate each time, and the combined organic phases are washed once each with saturated sodium hydrogencarbonate solution and saturated sodium chloride solution, dried over magnesium sulphate and concentrated in vacuo. The residue is chromatographed on a column (80 g of silica gel 230–400 mesh, diameter 2.5 cm, with ethyl acetate/petroleum ether 1:1).

Yield: 200 mg (41.1% of theory)

$^1$H NMR (CDCl$_3$): δ=1.25 (m, 12H); 1.43 (m, 2H); 2.42 (m, 2H); 3.32 (sept. 1H); 3.58 (m, 1H); 3.73 (s, 3H); 3.81 (s, 3H); 4.08 (m, 1H); 4.32 (m, 1H); 5.28 (dd, 1H); 6.33 (d, 1H); 7.0–7.1 (m, 4H); 7.77 (s, 1H) ppm.

Example 7

Sodium erythro-(E)-7-[2,6-diisopropyl-4-(4-fluorophenyl)5-methoxyiminomethyl-pyrid-3-yl]-3,5-dihydroxy-hept-6-enoate

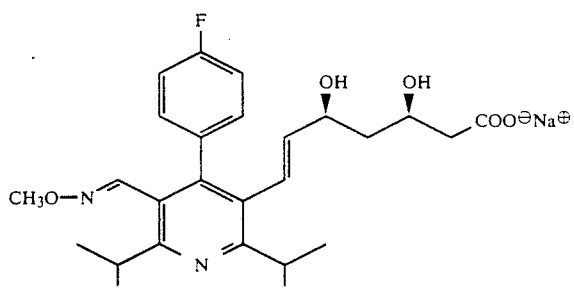

150 mg (0.3 mmol) of the compound from Example 6 are dissolved in 10 ml of tetrahydrofuran and 3 ml of 0.1 N sodium hydroxide solution are added. After 1 hour, the tetrahydrofuran is stripped off in vacuo and the aqueous residue is freeze-dried.

Yield: 143 mg (97% of theory)

¹H NMR (CDCl₃): δ=0.89 (m, 1H); 1.22 (m, 12H); 1.32 (m, 1H); 1.27 (dd, 1H); 1.95 (dd, 1H); 3.31 (s, 3H); 3.38 (sept., 1H); 3.52 (sept., 1H); 4.03 (m, 1H); 4.92 (m, 1H); 5.31 (dd, 1H); 6.18 (d, 1H); 7.0–7.3 (m, 4H); 7.78 (s, 1H) ppm.

Example 8

Trans-(E)-6-[2-(2,6-diisopropyl-4-(4-fluorophenyl)-3-methoxyiminomethyl-pyrid-5-yl)-ethenyl]-3,4,5,6-tetrahydro-4-hydroxy-2H-pyran-2-one

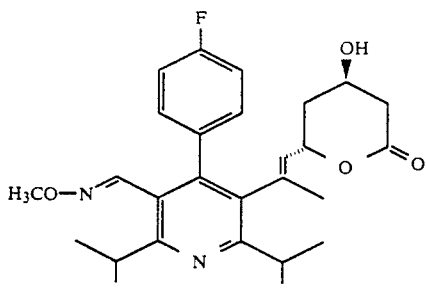

40 mg (0.08 mmol) of the compound from Example 6 are dissolved in 10 ml of tetrahydrofuran and, after addition of 0.8 ml (0.08 mmol) of 0.1 N sodium hydroxide solution, the mixture is stirred at room temperature for 1 hour. It is then diluted with 10 ml of water, adjusted to pH 4.4 with 1 N hydrochloric acid and extracted several times with methylene chloride. The combined organic phases are dried with sodium sulphate and concentrated in vacuo. The residue is dissolved in 20 ml of absolute toluene and, after addition of 5 g of molecular sieve 4 Å, the solution is heated under reflux overnight. Molecular sieve is then filtered off, and the filtrate is concentrated and filtered through a short silica gel column (eluent ethyl acetate/petroleum ether 1 1).

Yield: 21.1 mg (58.1% of theory)

¹H NMR (CDCl₃): δ=1.28 (m, 12H); 1.4–1.9 (m, 2H); 2.6 (m, 2H); 3.31 (sept., 1H); 3.57 (sept., 1H); 3.82 (s, 3H); 4.18 (m, 1H); 5.08 (m, 1H) 5.32 (dd, 1H); 6.42 (d, 1H); 7.0–7.2 (m, 4H); 7.77 (s, 1H) ppm.

Example 9

3-Benzyloxyiminomethyl-5-tert.-butyldimethylsilyloxymethyl-2, 6-diisopropyl-4-(4-fluorophenyl)-pyridine

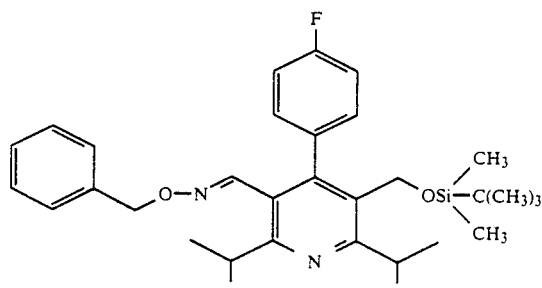

The title compound is obtained from 2.1 g (5 mmol) of the compound from Example VII and 922.5 mg (7.5 mmol) of benzylhydroxylamine hydrochloride analogously to Example 1.

Yield 1.55 g (57% of theory) ¹H NMR (CDCl₃): δ=0.01 (s, 6H); 0.91 (s, 9H); 1.28 (d, 6H); 1.39 (d, 6H); 3.50 (m, 2H); 4.37 (s, 2H); 5.13 (s, 2H); 7.0–7.5 (m, 9H); 7.87 (s, 1H) ppm.

Example 10

Methyl erythro-(E)-7-[5-benzyloxyiminomethyl-2,6-diisopropyl-4-(4-fluorophenyl) -pyrid-3-yl]-3,5-dihydroxy-hept6-enoate

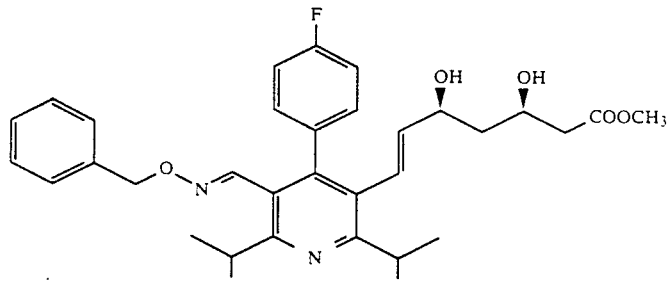

Example 10 is prepared from the compound of Example 9, in analogy to the reactions of Examples 2–6. ¹H NMR (CDCl₃): δ=1.26 (m, 12H); 1.42 (m, 2H); 2.43 (m, 2H); 3.31 (sept., 1H); 3.44 (sept., 1H); 3.72 (s, 3H); 4.08 (m, 1H); 4.30 (m, 1H); 5.05 (s, 2H); 5.26 (dd, 1H); 6.30 (d, 1H); 6.98 (m, 4H); 7.2–7.4 (m, 5H); 7.82 (s, 1H) ppm.

Example 11

3-tert.-Butoxyiminomethyl-5-tert.-butyldimethylsilyloxymethyl-2, 6-diisopropyl-4-(4-fluorophenyl)-pyridine

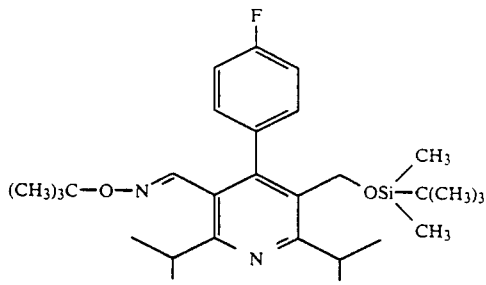

The title

The title compound is obtained from 2 1 g (5 mmol) of the compound from Example VII and 941 mg (7.5 mmol) of o-tert.-butylhydroxylamine hydrochloride analogously to Example 1.

Yield 770 mg (30.8% of theory)

$^1$H NMR (CDCl$_3$): δ=0.0 (s, 6H); 0.89 (s, 9H); 1.28 (s, 9H); 1.40 (m, 6H); 3.48 (sept., 1H); 3.63 (sept., 1H); 4.37 (s, 2H); 7.1–7.3 (m, 4H); 7.82 (s, 1H) ppm.

Example 12

Methyl erythro-(E)-7-[5-tert.-butyloxyiminomethyl-2,6-diisopropyl-4-(4-fluorophenyl)-pyrid-3-yl]-3,5-dihydroxyhept-6-enoate

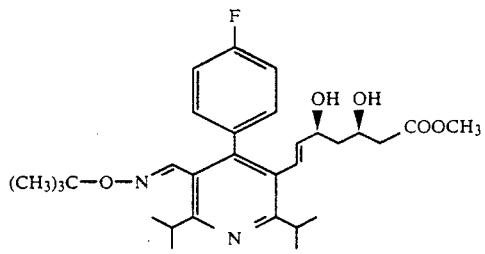

Example 12 was prepared from the compound of Example 11, in analogy to the reactions of Examples 2–6. $^1$H NMR (CDCl$_3$): δ=1.1–1.3 (m, 21H); 1.42 (m, 2H); 2.42 (m, 2H); 3.32 (sept., 1H); 3.53 (sept., 1H); 3.73 (s, 3H); 4.08 (m, 1H); 4.30 (m, 1H); 5.28 (dd, 1H) 6.31 (d, 1H); 7.0–7.1 (m, 4H); 7.78 (s, 1H) ppm.

It is understood that the specification and examples are illustrative but not limitative of the present invention and that other embodiments within the spirit and scope of the invention will suggest themselves to those skilled in the art.

We claim:

1. An imino-substituted pyridine of the formula

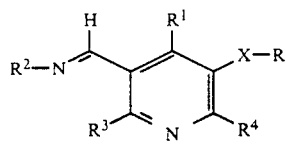

in which
- $R^1$ represents aryl having 6 to 10 carbon atoms, which is optionally monosubstituted to trisubstituted by identical or different substituents from the group consisting of halogen, hydroxyl, trifluoromethyl, trifluoromethoxy, nitro, cyano, straight-chain or branched alkyl or alkoxy in each case having up to 8 carbon atoms and aryloxy having 6 to 10 carbon atoms,
- represents aryl having 6 to 10 carbon atoms, which is optionally monosubstituted to trisubstituted by identical or different substituents from the group consisting of straight-chain or branched alkyl in each case having up to 8 carbon atoms, halogen, cyano, trifluoromethyl, trifluoromethoxy and nitro, or represents straight-chain or branched alkyl having up to 10 carbon atoms, which is optionally substituted by aryl having 6 to 10 carbon atoms, hydroxyl or alkoxy having up to 8 carbon atoms, or represents a group of the formula —$R^5$, in which
- $R^5$ denotes hydrogen or straight-chain or branched alkyl having up to 8 carbon atoms, which is optionally substituted by aryl having 6 to 10 carbon atoms, or denotes aryl having 6 to 10 carbon atoms, which is optionally substituted by straight-chain or branched alkyl or alkoxy in each case having up to 8 carbon atoms, halogen, nitro, cyano, trifluoromethyl or trifluoromethoxy,
- represents cycloalkyl having 3 to 8 carbon atoms, or represents aryl having 6 to 10 carbon atoms, which is optionally monosubstituted to trisubstituted by identical or different substituents from the group consisting of halogen and straight-chain or branched alkyl having up to 8 carbon atoms, or represents straight-chain or branched alkyl having up to 10 carbon atoms, which is optionally substituted by a group of the formula —$R^5$, in which $R^5$ has the abovementioned meaning,
- $R^4$ represents straight-chain or branched alkyl having up to 10 carbon atoms, or represents cycloalkyl, having 3 to 8 carbon atoms,
- X represents a group of the formula —CH$_2$—CH$_2$— or —CH=CH—, and
- R represents a group of the formula

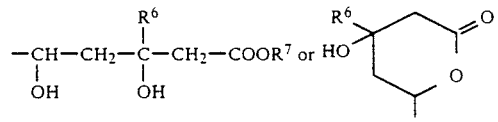

in which
- $R^6$ denotes hydrogen or straight-chain or branched alkyl having up to 10 carbon atoms and
- $R^7$ denotes hydrogen or straight-chain or branched alkyl having up to 10 carbon atoms, which may be substituted by phenyl, or denotes aryl having 6 to 10 carbon atoms or a cation, or a salt thereof.

2. An imino-substituted pyridine or salt thereof according to claim 1, in which
- $R^1$ represents phenyl which is optionally monosubstituted or disubstituted by identical or different substituents from the group consisting of fluorine, chlorine, bromine, hydroxyl, straight-chain or branched alkyl or alkoxy in each case having up to 6 carbon atoms and phenoxy,
- $R^2$ represents phenyl which is optionally monosubstituted or disubstituted by identical or different substituents from the group consisting of fluorine, chlorine, bromine and straight-chain or branched alkyl having up to 6 carbon atoms, or represents straight-chain or branched alkyl having up to 8 carbon atoms, which is optionally substituted by phenyl or alkoxy having up to 6 carbon atoms, or represents a group of the formula —O$R^5$ in which
- $R^5$ denotes hydrogen or straight-chain or branched alkyl having up to 6 carbon atoms, which is optionally substituted by phenyl, or denotes phenyl which is optionally substituted by straight-chain or branched alkyl or alkoxy in each case having up to 6 carbon atoms,
- $R^3$ represents cyclopropyl, cyclobutyl, cyclopentyl or cyclohexyl, or represents phenyl which is optionally monosubstituted or disubstituted by identical or different substituents from the group consisting of fluorine, chlorine, bromine and straight-chain or branched alkyl having up to 6 carbon atoms, or represents straight-chain or branched alkyl having up to 8 carbon atoms, which is optionally substituted by a group of the formula —OR$^5$ in which R$^5$ has the abovementioned meaning, R$^4$ represents straight-chain or branched alkyl having up to 8 carbon atoms, or represents cyclopropyl, cyclopentyl or cyclohexyl, X represents a group of the formula —CH$_2$—CH$_2$— or —CH=CH— and R represents a group of the formula

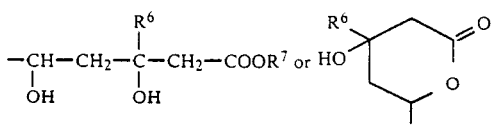

in which

R$^6$ denotes hydrogen or straight-chain or branched alkyl having up to 8 carbon atoms and R$^7$ denotes hydrogen or straight-chain or branched alkyl having up to 8 carbon atoms or benzyl, or denotes phenyl or a cation.

3. An imino-substituted pyridine or salt thereof according to claim 1, in which

R$^1$ represents phenyl which is optionally substituted by fluorine, chlorine, straight-chain or branched alkyl having up to 4 carbon atoms or phenoxy, or R$^2$ represents a group of the formula —OR$^5$ in which R$^5$ denotes hydrogen, benzyl or straight-chain or branched alkyl having up to 4 carbon atoms or denotes phenyl, R$^3$ represents cyclopropyl or phenyl, or represents a straight-chain or branched alkyl having up to 6 carbon atoms, which is optionally substituted by a group of the formula —OR$^5$ in which R$^5$ the abovementioned meaning, R$^4$ represents straight-chain or branched alkyl having up to 6 carbon atoms or cyclopropyl, X represents the group —CH=CH— and R represents a group of the formula

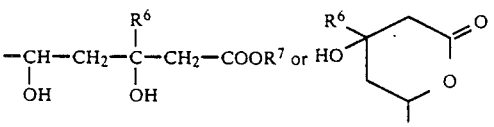

in which

R$^6$ denotes hydrogen, methyl, ethyl, propyl, isopropyl, butyl, isobutyl or tert.butyl and R$^7$ denotes hydrogen, methyl, ethyl, propyl, isopropyl, butyl, isobutyl, tert.butyl or benzyl, or denotes a sodium, potassium, calcium, magnesium or ammonium ion.

4. An aminosubstituted pyridine or salt thereof according to claim 3, in which R$^6$ is hydrogen.

5. A compound according to claim 1, wherein such compound is methyl erythro-(E)-7-[2,6-diisopropyl-4-(4-fluorophenyl)5-methoxyiminomethyl-pyrid-3-yl]-3,5-dihydroxy-hept-6-enoate of the formula

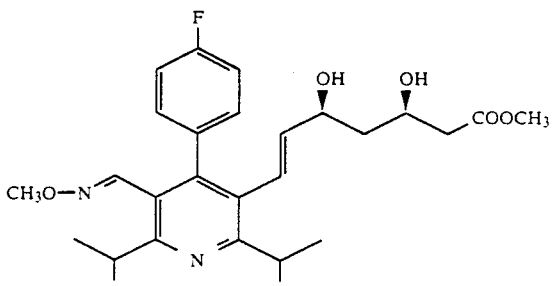

or a salt thereof.

6. A compound according to claim 1, wherein such compound is erythro-(E)-7-[2,6-diisopropyl-4-(4-fluorophenyl)-methoxyiminomethyl-pyrid-3-yl]-3,5-dihydroxy-hept-6-enoic acid of the formula

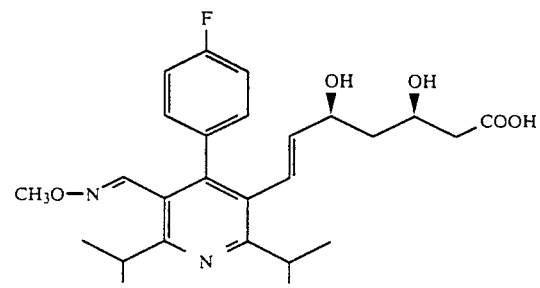

or a salt thereof.

7. A compound according to claim 1, wherein such compound is trans-(E)-6-[2-(2,6-diisopropyl-4-(4-fluorophenyl)-3-methoximinomethyl-pyrid-5-yl) -ethenyl]-3,4,5,6-tetrahydro-4-hydroxy-2H-pyran-2-one of the formula

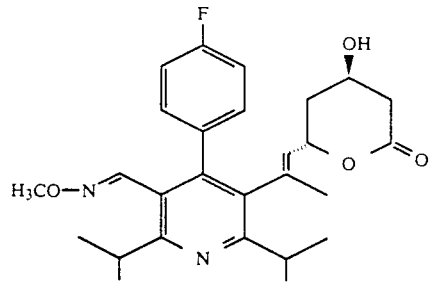

or a salt thereof.

8. A composition for the treatment of hyperlipoprotein-aemia, lipoproteinaemia or atherosclerosis comprising an amount effective therefor of a compound or salt according to claim 1 and a diluent.

9. A method of treating hyperlipoproteinaemia, lipoproteinaemia or atherosclerosis in a patient in need thereof which comprises administering to such patent an amount effective therefor of a compound or salt according to claim 1.

10. The method according to claim 9, wherein such compound is methyl erythro-(E)-7-[2,6-diisopropyl-4-(4-fluorophenyl) -5-methoxyiminomethyl-pyrid3-yl]-3,5-dihydroxy-hept-6-enoate, erythro-(E)-7-[2,6-diisopropyl-4-(4-fluorophenyl) -5-methoxyiminomethyl-pyrid-3-yl]-3,5dihydroxy-hept-6-enoic acid or trans-(E)-6-[2-(2,6-diisopropyl-4-(4-fluorophenyl)3-methoximinomethyl-pyrid-5-yl) -ethenyl]-3,4,5,6-tetrahydro-4-hydroxy-2H-pyran-2-one, or a salt thereof.

* * * * *

UNITED STATES PATENT AND TRADEMARK OFFICE
CERTIFICATE OF CORRECTION

PATENT NO. : 5,064,841

DATED : November 12, 1991

INVENTOR(S) : Angerbauer et al.

It is certified that error appears in the above-identified patent and that said Letters Patent is hereby corrected as shown below:

| | |
|---|---|
| Title Page | ABSTRACT: Line 8 delete " aaryl " and substitute -- aryl --, line 10 delete " $\leq$ " and substitute -- - --. |
| Col. 29, line 58 | Before " represents " insert -- $R^2$ -- |
| Col. 29, last line | Delete " - --$R^5$ " and substitute -- $-OR^5$ -- |
| Col. 30, line 10 | Before " represents " insert -- $R^3$ -- |
| Col. 30, line 18 | Delete " - --$R^5$" and substitute -- $-OR^5$ -- |
| Col. 31, line 37 | After " represents " delete " a " |
| Col. 31, line 41 | After " $R^5$ " insert -- has -- |
| Col. 31, claim 4 line 1 | Delete " aminosubstituted " and substitute --imino-substituted -- |

Signed and Sealed this

Fifteenth Day of June, 1993

Attest:

MICHAEL K. KIRK

*Attesting Officer*     Acting Commissioner of Patents and Trademarks